(12) United States Patent
Liu

(10) Patent No.: US 6,291,816 B1
(45) Date of Patent: Sep. 18, 2001

(54) SYSTEM AND METHOD FOR MEASURING OBJECT FEATURES WITH COORDINATED TWO AND THREE DIMENSIONAL IMAGING

(75) Inventor: Kuo-Ching Liu, New York, NY (US)

(73) Assignee: Robotic Vision Systems, Inc., Hauppauge, NY (US)

( * ) Notice: Subject to any disclaimer, the term of this patent is extended or adjusted under 35 U.S.C. 154(b) by 0 days.

(21) Appl. No.: 09/327,817

(22) Filed: Jun. 8, 1999

(51) Int. Cl.[7] ................................................. G01B 11/00
(52) U.S. Cl. ..................... 250/234; 250/559.06; 356/608
(58) Field of Search ................................. 250/234–236, 250/559.04–559.06, 559.23, 559.31, 559.34, 559.48, 559.49; 356/375, 608; 359/201, 202

(56) References Cited

U.S. PATENT DOCUMENTS

| 5,554,858 | * | 9/1996 | Costa et al. ................. 250/559.29 |
| 5,859,924 | * | 1/1999 | Liu et al. ........................... 356/375 |
| 6,031,225 | * | 2/2000 | Stern et al. ...................... 250/235 |

* cited by examiner

*Primary Examiner*—Stephone B. Allen
(74) *Attorney, Agent, or Firm*—Kenyon & Kenyon

(57) ABSTRACT

A system and method are disclosed for highly efficient imaging of selected object features utilizing, in combination, a 2D imaging subsystem and a 3D imaging subsystem wherein data from the 2D imaging subsystem is used to predetermine areas containing 3D features of interest such that delay attributable to imaging of areas of non-interest for 3D features is minimized.

19 Claims, 8 Drawing Sheets

SYSTEM AND METHOD FOR MEASURING OBJECT FEATURES WITH COORDINATED TWO AND THREE DIMENSIONAL IMAGING

FIELD OF INVENTION

The present invention is directed to a method and system for imaging selected physical dimensions of an object. In particular, the present invention is directed to highly efficient systems for and methods of two and three dimensional imaging of selected features of an object. Specifically, the methods and systems may be utilized for, among other things, the measurement of critical physical dimensions of semiconductor wafers used in the fabrication of microelectronic devices.

COPYRIGHT NOTICE

A portion of the disclosure of this patent document contains material which is subject to copyright protection. The copyright owner has no objection to the facsimile reproduction by anyone of the patent document or patent disclosure as it appears in the patent and Trademark Office, patent file or records, but otherwise reserves all copyright rights whatsoever.

BACKGROUND INFORMATION

In the continuing effort to produce smaller electronic devices, manufacturers of such devices are, in some circumstances, dispensing with the packaging material which forms a large part of the volume of a typical chip. An example of such technology is the so called "flip chip" device. Balls of solder are applied directly to the underside of the sections of wafer destined to be electronic chips, which sections are known as dies. These solder balls allow direct connection of each flip chip after the wafer is cut into individual devices. The facilitation of external connections is thus moved from the back end (packaging) to the front end (wafer fabrication) of a microelectronic device production line. Where high volume, high efficiency production is required, as in the manufacture of flip chip ball grid array (FC-BGA) devices, a need exists for rapid and accurate measurement of the solder balls or bumps.

Systems are known for separate two dimensional (2D) and three dimensional (3D) imaging of object features. A two dimensional imaging system can provide information regarding whether or not a part of an object covers a certain X-Y point in space. For example, on a flip chip device a 2D imaging system would determine the maximum extent of the hemispherically shaped volume of solder comprising a ball as projected in the X-Y plane. Thus, a 2D system would obtain data indicating that a circular shaped region of the X-Y plane was covered by the ball. Such a 2D system collects no information regarding the height, or Z dimension, of the ball. Such 2D measuring systems generally use charged coupled devices (CCDs) and can rapidly and simultaneously collect 2D data for a selected region of a target object. Such 2D systems have the advantage of high speed collection but obviously lack information on the Z dimension.

A 3D imaging system can collect X, Y and Z data regarding dimensions of a target object. For the example of a single ball of a flip chip device, a 3D system would obtain data containing the height of the ball at each X-Y point or equivalently, the X-Y extent of the ball at each height Z. Such 3D data is generally collected by directing one or more laser beams over the surface of the target object with data for each laser beam collected sequentially by a CCD or position sensitive device (PSD). Such devices usually rely on optical triangulation techniques. While the systems provide full 3D data, they are much slower than 2D systems due to the volume of the extra data and the sequential method of collection.

Three dimensional optical sensor systems utilizing laser optical triangulation have been used to inspect chip packages. Such a system typically consists of a semiconductor diode laser, a beam deflector (for example, an acousto-optical (AO) deflector, also called an AO modulator) and a position sensitive device (PSD). The laser diode provides the light source for measurements. The beam deflector directs the laser beam to sweep the directed light over a narrow strip of area on the target object. To cover the entire target area, such systems typically rely on a mechanical translation, of the target object, or in some circumstances, the sensor system, in a direction perpendicular to the AO sweep direction. The PSD measures the height of the target object at each scan point and the data are stored until an image record for the entire object or a selected portion is collected. The stored image record may then be compared to a manufacturer's specification for the object or a selected portion thereof to determine whether the object or portion of interest meets specification.

Note that while systems such as those described herein are often generally referred to as "scanners" or "scanning systems", as used herein, the terms "scan" and "scanning" refer to the steps of directing light upon a target object and collecting light reflected from the target object into a photodetector to generate one or more electrical signals that are stored in a memory device, or buffer. This definition provides a distinction from the subsequent processing steps applied to these stored raw data to generate an image or to perform any other analysis required such as comparing the data to manufacturer specifications.

As used herein, the term "image" (a noun) refers to any collection of information in tangible form representing properties of an object where the data is categorized according to geometrical location. The term "image" (a verb), as used herein, may have two meanings depending on the context. It may refer to the overall process of scanning an object to obtain raw data followed by the processing of that data to produce an image. For example, "the object was imaged". Where the scanning step is distinguished from the overall process of producing an image of an object, the term "image" may refer only to the post-scanning processing of the raw data. For example, "the object was scanned and imaged". Accordingly, appreciation of the separability of the scanning and imaging phases of acquiring a final image of a target object is important to understanding the present invention.

U.S. Pat. No. 5,554,858 issued to Costa et al. ("Costa '858"), expressly incorporated herein by reference, describes a 3D imaging system. A laser light source combined with an AO deflector is positioned to illuminate an object and sweep along the AO deflection direction while commercially available linear motion tables provide the transverse translation. PSD sensors are positioned on both sides of the incident beam to receive light reflected from the sample and focused into the PSDs by lenses. Further, Costa '858 describes use of multi-channel PSDs to collect the imaging data. A PSD provides an analog output current ratio proportional to the position of a light spot falling along its length. A multi-channel PSD has a segmented photosensitive area, the multiple segments comprising the multiple data channels. When used with a selective sampling technique, the multi-channel PSD can reduce the effect of stray or multiply reflected light.

U.S. Pat. No. 5,859,924 to Liu et al. ("Liu '924"), expressly incorporated herein by reference, describes another such system. Liu '924 describes another imaging system utilizing optical triangulation techniques. This system uses a laser beam and AO deflector and one or more photosensitive devices to collect light reflected off-axially (from the axis of the incident light source) from the target object. Further, the system uses a polarizing beam splitter in the optical path of the incident beam to direct light reflected co-axially from the target object into a photo diode array for intensity measurement.

U.S. patent application Ser. No. 09/095,367 ("Liu App. '367"), filed Jun. 6, 1998, expressly incorporated herein by reference, describes a 3D scanning system in which multiple laser beams are swept across a sample by a beam deflector and the multiple reflected beams are imaged into one or more PSDs or CCDs for determination of a 3D profile of the target object.

U.S. patent application Ser. No. 09/019,479 ("Liu App. '479"), filed Feb. 5, 1998, expressly incorporated herein by reference, describes a system and method for selective scanning of an object or pattern including scan correction.

While the speed of 3D scanning has been improving, 3D scanning has still remained a process limiting step. It has therefore been desired to find ways to further increase the speed of acquiring desired 3D data about target objects.

SUMMARY OF THE INVENTION

The present invention is directed to a system for quickly and accurately measuring physical dimensions of selected object features. In many applications, such as the verification of compliance with manufacturing specifications of electronic components, such as flip chips, 3D data is not required for the entire area of an electronic component. Therefore, it is an object of the present invention to provide an imaging system that utilizes both a 2D and 3D imaging subsystem, the subsystems working cooperatively and in coordination to rapidly and efficiently collect desired data. It is an object of the present invention to provide an imaging system that utilizes a 2D imaging subsystem to prescan a selected region of a object and utilizes a 3D imaging subsystem to 3D image subregions of the object selected by real-time analysis of the 2D prescan data. It is a further object to provide a system which utilizes the 2D prescan data to direct the 3D scanning and/or analysis of subregions of the previously 2D scanned region to more quickly measure the subregions requiring 3D imaging. It is a further object to provide a multi-mode imaging system which can perform only 2D or 3D imaging as desired or perform cooperative, coordinated 2D and 3D imaging to measure selected object features efficiently with the appropriate 2D or 3D data structure.

Collected 2D and/or 3D information can be compared to manufacturer's specifications for example, for a flip chip, to determine if, for example, each solder ball or bump on the device is within tolerance for height and location. Additionally, the information can be used for determining co-planarity of the ball tops in a die and/or warpage of the wafer.

BRIEF DESCRIPTION OF THE DRAWINGS

The foregoing and other features of the present invention will be more readily apparent from the following detailed description of exemplary embodiments taken in conjunction with the attached drawings wherein.

DETAILED DESCRIPTION

Figure 1:
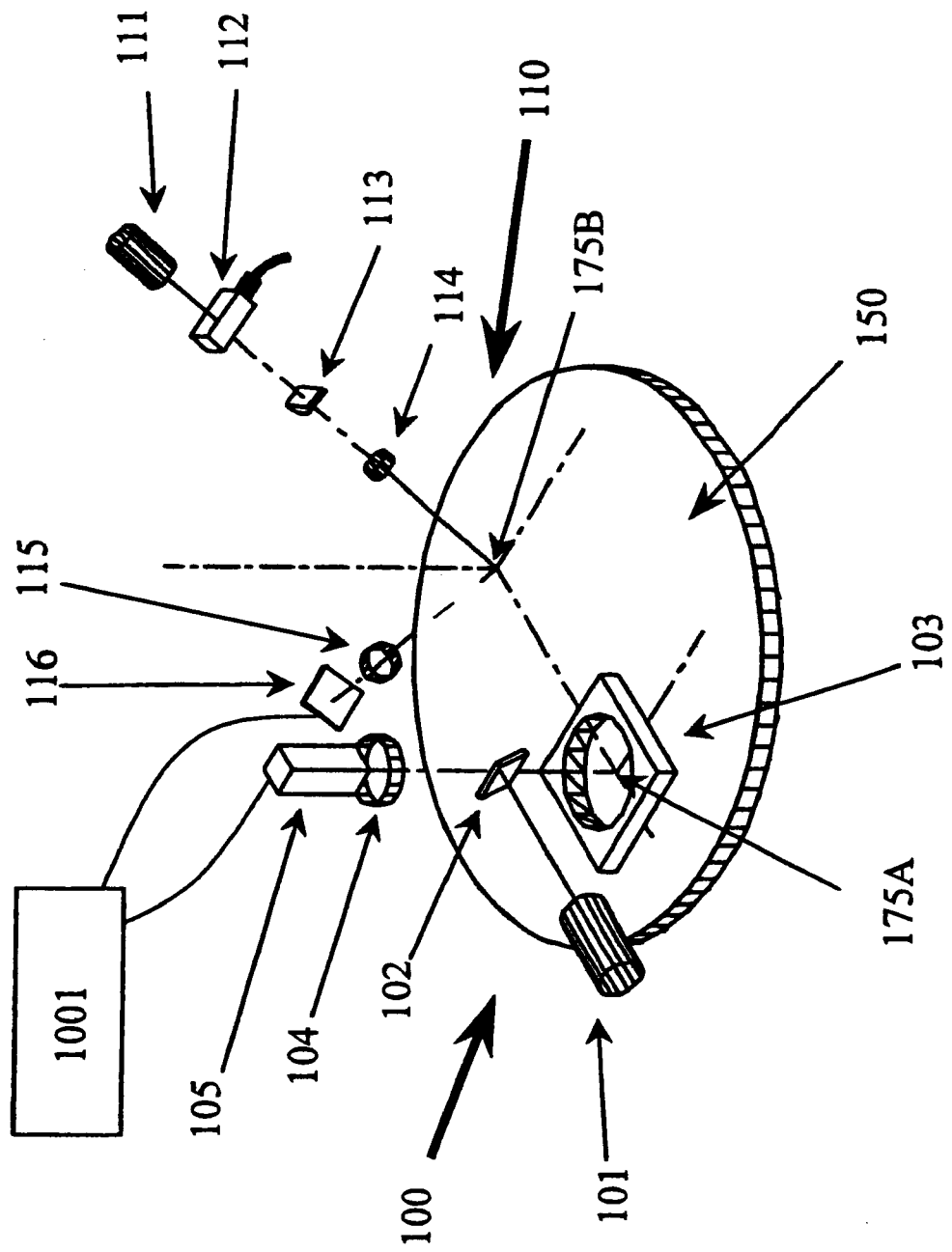
FIG. 1 is a perspective schematic view of an embodiment of a system in accord with the present invention.
Figure 2:
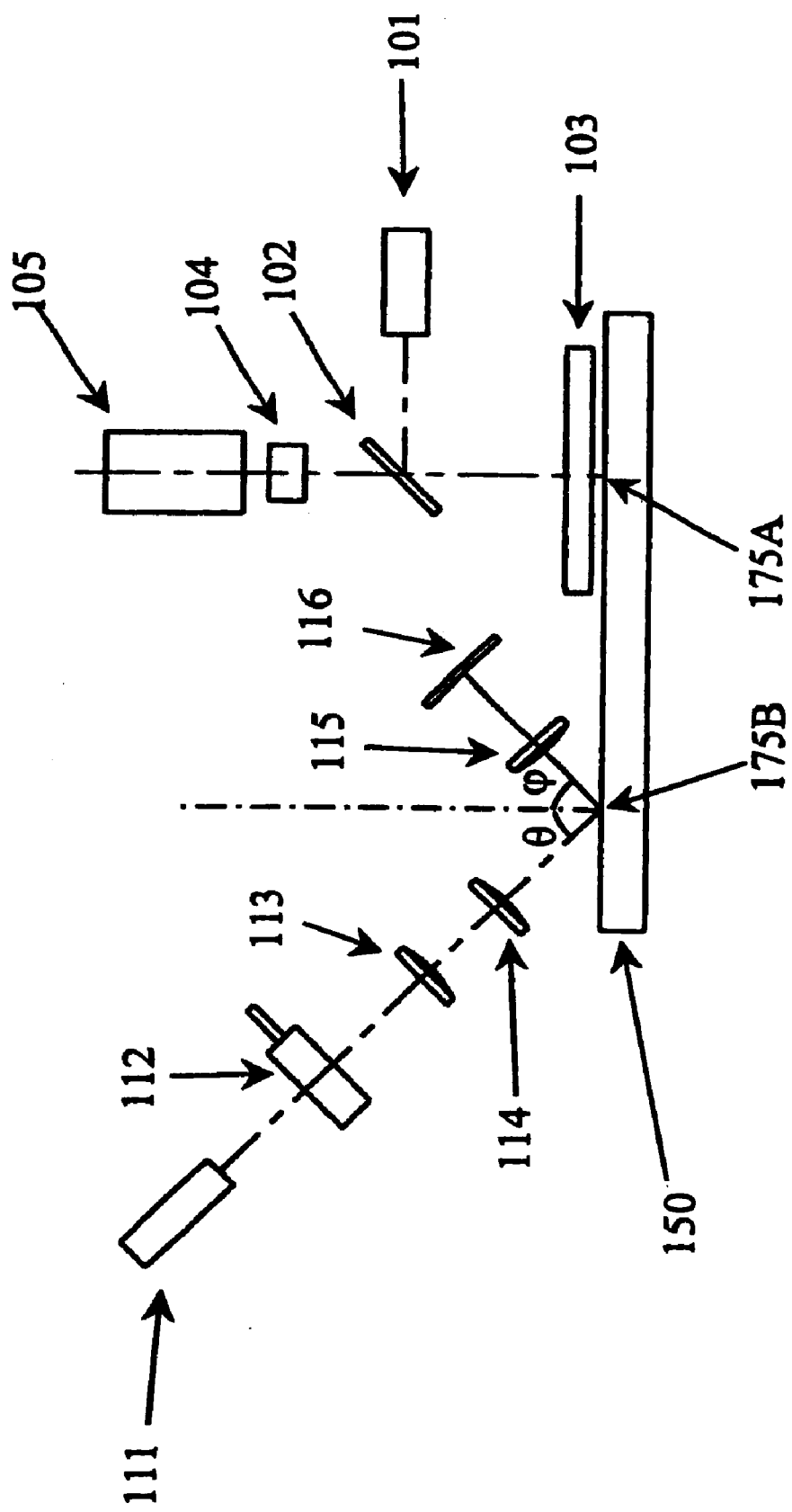
FIG. 2 is a schematic side view of the embodiment depicted in FIG. 1.

FIG. 1 and FIG. 2 schematically illustrate one embodiment of a system according to the present invention. The system has a 2D scanning assembly 100 and a 3D scanning assembly 110 represented schematically by their principal functioning components. The design and manufacture of suitable structures for positioning and fixing these functional components is known in the art. Scanning assembly 100 and scanning assembly 110 are respectively parts of the 2D and 3D imaging subsystems which in one embodiment of the invention are capable of operating to provide only 2D or 3D data if that is desired for a particular application. The acquisition and processing of data with such single mode systems is known in the art.

In an exemplary embodiment 2D and 3D imaging subsystems are capable of operating in cooperative coordination to obtain 2D data for all regions scanned and to obtain 3D data for only selected subregions of the 2D scanned regions. With reference to FIGS. 1 and 2, the operation of the individual imaging subsystems as known in the prior art will be described before the cooperative coordinated operation of a system in accord with the present invention is described. Accordingly, in FIGS. 1 and 2, an object, for example, wafer 150, is imaged to determine the dimensions of its upper surface features. Scanning assembly 100 is a representative 2D scanning assembly. A bright field illuminator 101 produces light which is reflected downward by beam splitter 102. This light impinges upon the wafer normal to the wafer plane at target position 175A. Dark field illuminator 103 also directs light upon the wafer surface at target position 175A. The dark field illuminator may consist, for example, of a ring of light emitting diodes which encompass the specific target area to provide dark field illumination. Some light from the light and dark field illuminators is reflected from the wafer surface at 175A, passes through beam splitter 102 and is focused by focusing element 104 onto detector 105, for example, a CCD detector. The raw data from the 2D detector is processed in control and analysis subsystem 1001. In a typical arrangement, either the target object or the scanning assembly is translated mechanically as described above. It should be appreciated that the 2D and 3D imaging subsystems each consist of a scanning assembly and controller comprising hardware and software or firmware. The controller controls the movement of the target object or scanning assembly, analyzes the measured data and coordinates the movement and data acquisition. Controller 1001 generically represents the computing hardware and software or firmware which performs data manipulation and controls any motion of the target object or scanning assembly.

Further, with reference to FIGS. 1 and 2, scanning assembly 110 is a representative 3D scanning assembly. A light source 111, typically a diode laser, produces light directed through an AO deflector 112. The light passes through optical elements 113 and 114 and is focused upon the target region of the object surface at target position 175B. Some light is reflected through optical element 115 and is focused onto detector 116, typically a PSD. The angle of incidence $\theta$ is equal to the angle of reflection $\phi$ so that the PSD receives bright field illumination. The AO deflector causes the laser light to sweep a segment of the target region as described above. The raw data from the 3D detector is processed in controller 1001. Controller 1001 similarly controls any movement of the target object or scanning assembly and performs data analysis. Controller 1001 would also control any electrically active optical components such as the AO deflector. It should be appreciated that the respective control and analysis means for the 2D and 3D subsystems may be integrated or physically separated within the scope of generic controller 1001 without departing from the present invention.

In the embodiment depicted in FIGS. 1 and 2, it should be appreciated that scanning assemblies 100 and 110 are not coaxially aligned. That is, the functional components of the respective scanning assemblies are positioned and directed such that the target positions 175A and 175B are different at any given moment regardless of whether the illumination components are actually turned on at that time. In this embodiment, to obtain both a 2D and 3D image of the same target position, the relative position of the target object with respect to both scanning assemblies should be changed. In other words, the desired target position on the target object should be moved from the focus of one scanning system to the focus of the other to obtain the respective scans.

Figure 3:
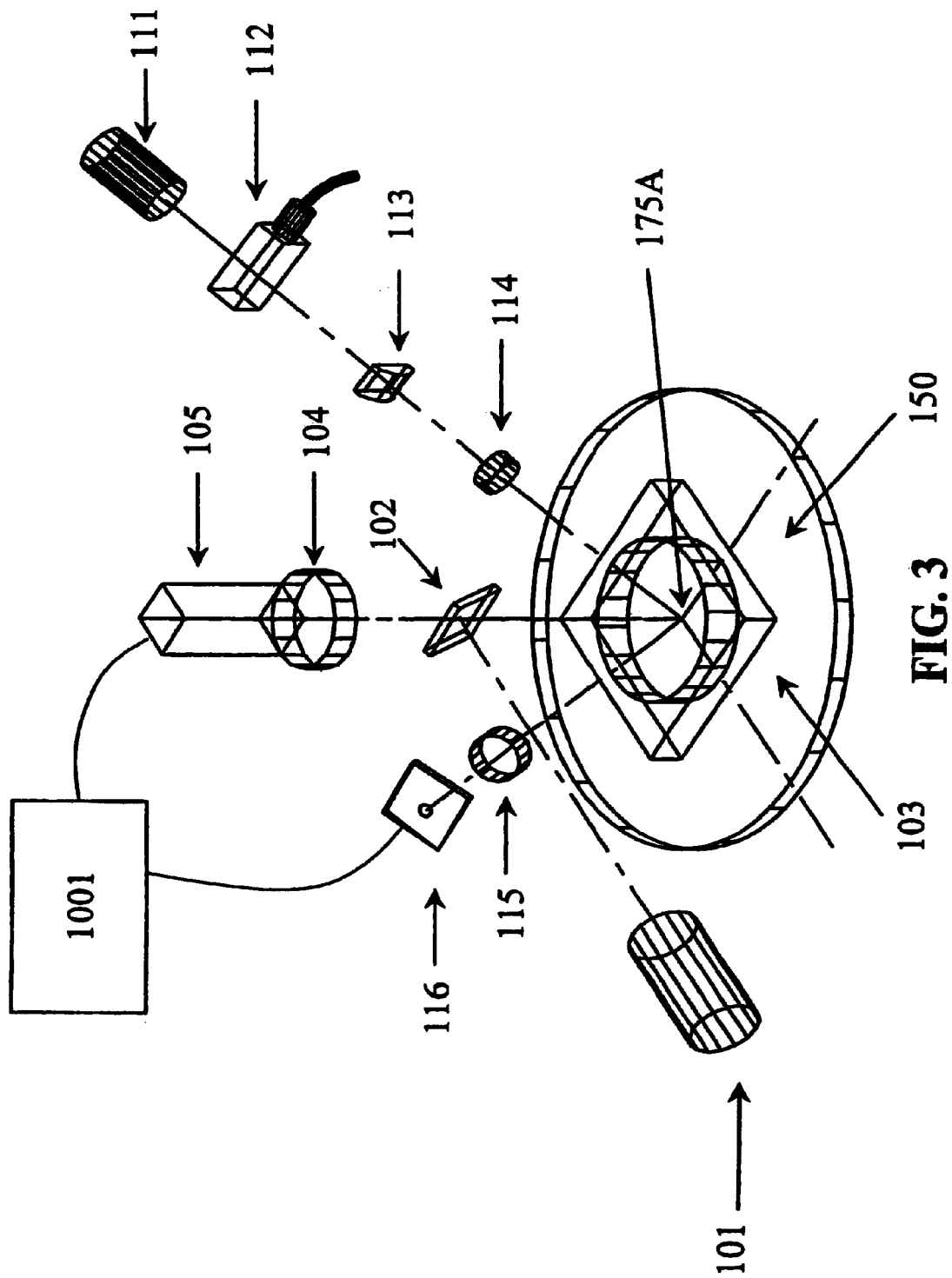
FIG. 3 is a schematic perspective view of another embodiment of a system in accord with the present invention.

FIG. 3 illustrates another embodiment of a system in accord with the present invention in which the 2D and 3D scanning assemblies are disposed coaxially. The functional components of the respective scanning assemblies are positioned and directed such that target positions 175A and 175B are coincident as depicted in FIG. 3. The coaxial and non-coaxial embodiments function very similarly. Distinctions between the operation of the two embodiments are noted in the discussion hereafter.

Preliminarily, it should be appreciated that in the processes for imaging an object described above, there are two general phases whether 2D or 3D imaging is involved. The two general phases are the data collection phase and the data processing phase. In the data collection phase, the target is illuminated and light reflected from the object is collected by a detector and stored into a memory device. In the data processing phase, the stored data is analyzed to determine relevant object dimensions and perform any additional desired analyzes such as comparison to manufacturer specifications.

Figure 4B:
FIG. 4A and 4B illustrate the arrangement of pixels in two exemplary types of photodetectors suitable for use in the present invention.
Figure 4A:
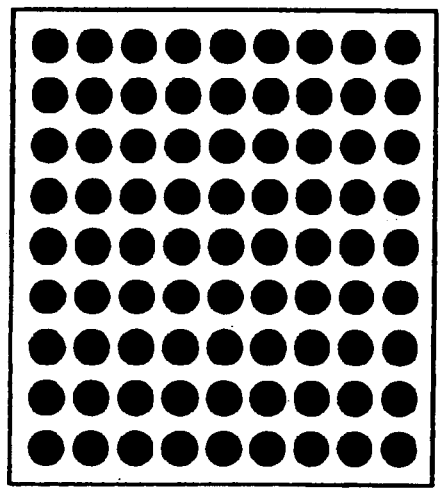

While the types of detectors for 2D and 3D data collection and their characteristics are known in the art, certain salient features are now described to allow better appreciation of the advantages of the present invention. For 2D data collection, CCD detectors are typically used and fall into two categories, i.e., area array cameras and line scan cameras. These are schematically represented in FIGS. 4A and 4B. FIG. 4A illustrates that in an area array camera, the individual CCD pixels are arranged in a rectangular, often square, configuration, or form factor. FIG. 4B illustrates that a line scan camera, as the name suggests, has the CCD pixels disposed in a linear configuration, or form factor. The particular 9±9 and 1±20 pixel configurations are merely illustrative. Actual area camera and line scan camera CCD devices typically have many more pixels. For example, a suitable line scan camera CCD device might have 2000 pixels, each pixel covers 5 $\mu$m in diameter on the target plane so that a 10 mm line is observed by this line scan camera with one measurement. A suitable area array camera might have 1000×1000 pixels with the same pixel size and coverage so that an area of 25 mm$^2$ is observed with one measurement. A method in accord with the present invention may be practiced with 2D detectors of either form factor with the details varying only slightly. With either form factor detector, the data is temporarily stored into a suitable frame buffer, or frame grabber, as it is recorded until the frame grabber is full.

Figure 5:
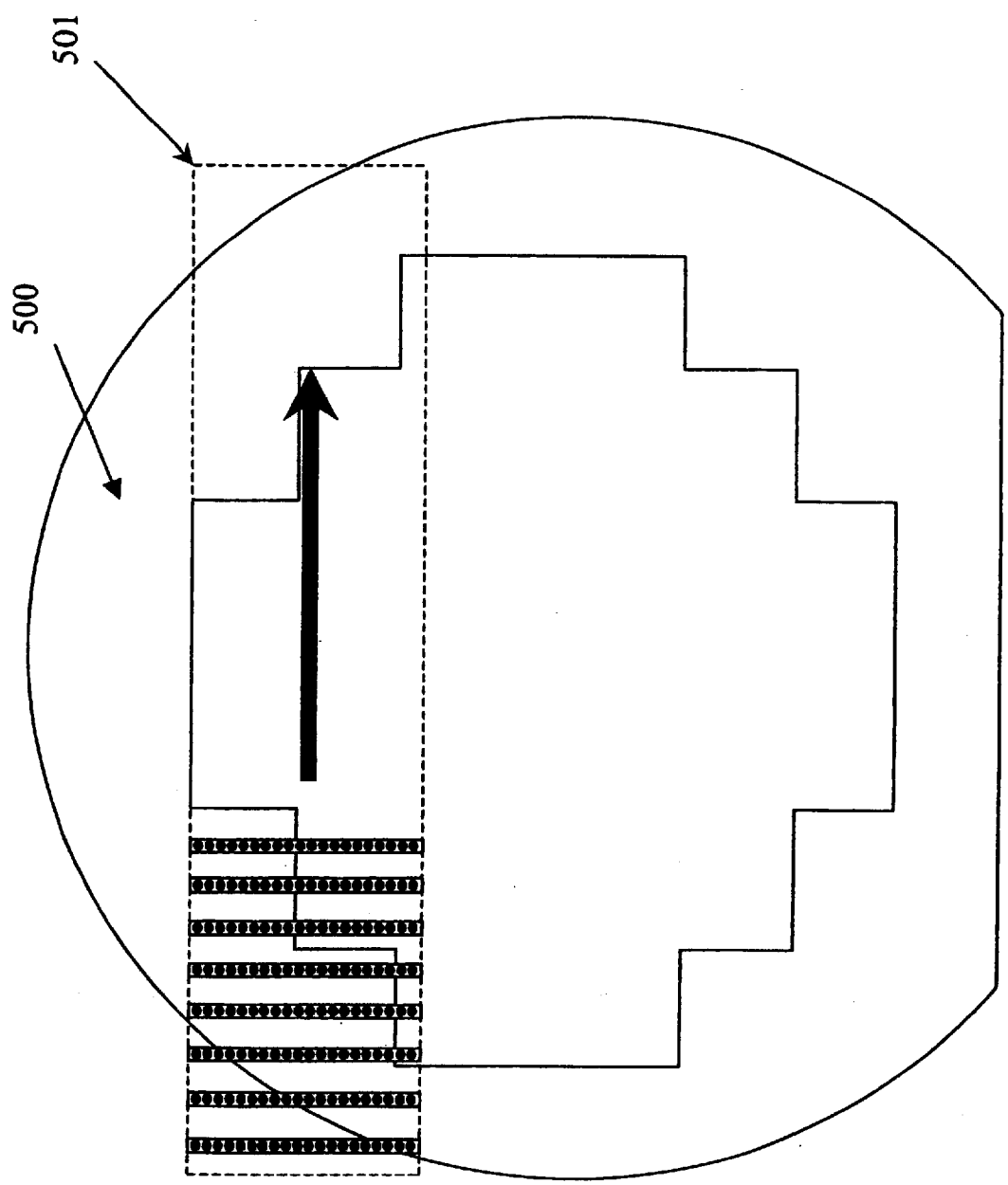
FIG. 5 illustrates a 2D prescan region on a target device being scanned with a line camera in an exemplary method in accord with the present invention.
Figure 6:
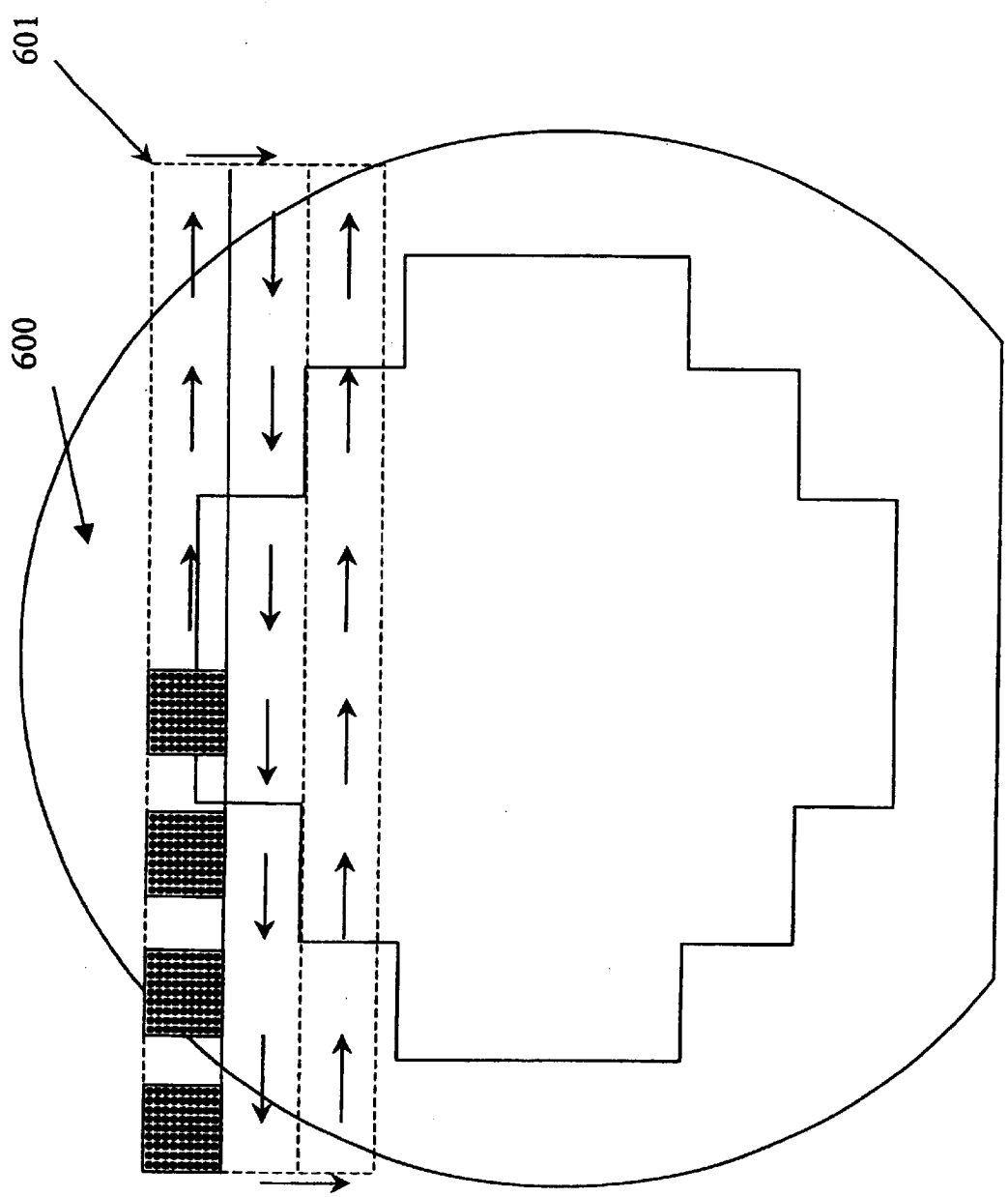
FIG. 6 illustrates a 2D prescan region on a target device being scanned with an area array camera in another exemplary method in accord with the present invention.

Accordingly, FIGS. 5 and 6 illustrate schematically how a wafer would be 2D scanned with, respectively, a line scan camera and an area array camera. In FIG. 5, target object region 501 on wafer 500 is 2D scanned by a line scan camera scanning consecutive positions from left to right. Note that for clarity of the drawing, only eight positions are shown and the positions are depicted much farther apart than they would be an actual embodiment. In practice the consecutive scanning positions of the 2D detector may be arranged to measure data in an equally spaced pixel pattern. An advantage of this line scan camera embodiment is that in one nearly continuous sweep from left to right (or equivalently right to left), the entire region 501 may be scanned. In operation, after one such sweep, the line scanning position would be changed to encompass another region, e.g., 502, and the entire wafer could be scanned in such fashion. In comparison, with reference to FIG. 6, it is seen that with an area array camera it may take more left-right scans to cover the same sized region 601 on wafer 600. In FIG. 6, the consecutive scanning positions are again depicted as farther apart than in actual practice for clarity of the figure. It should be appreciated that the comparison of FIGS. 5 and 6 would vary depending on the number of pixels and size of the respective line scan camera or area array camera. Criteria for selection of such 2D detectors are known to those of ordinary skill in the art.

Figure 7:
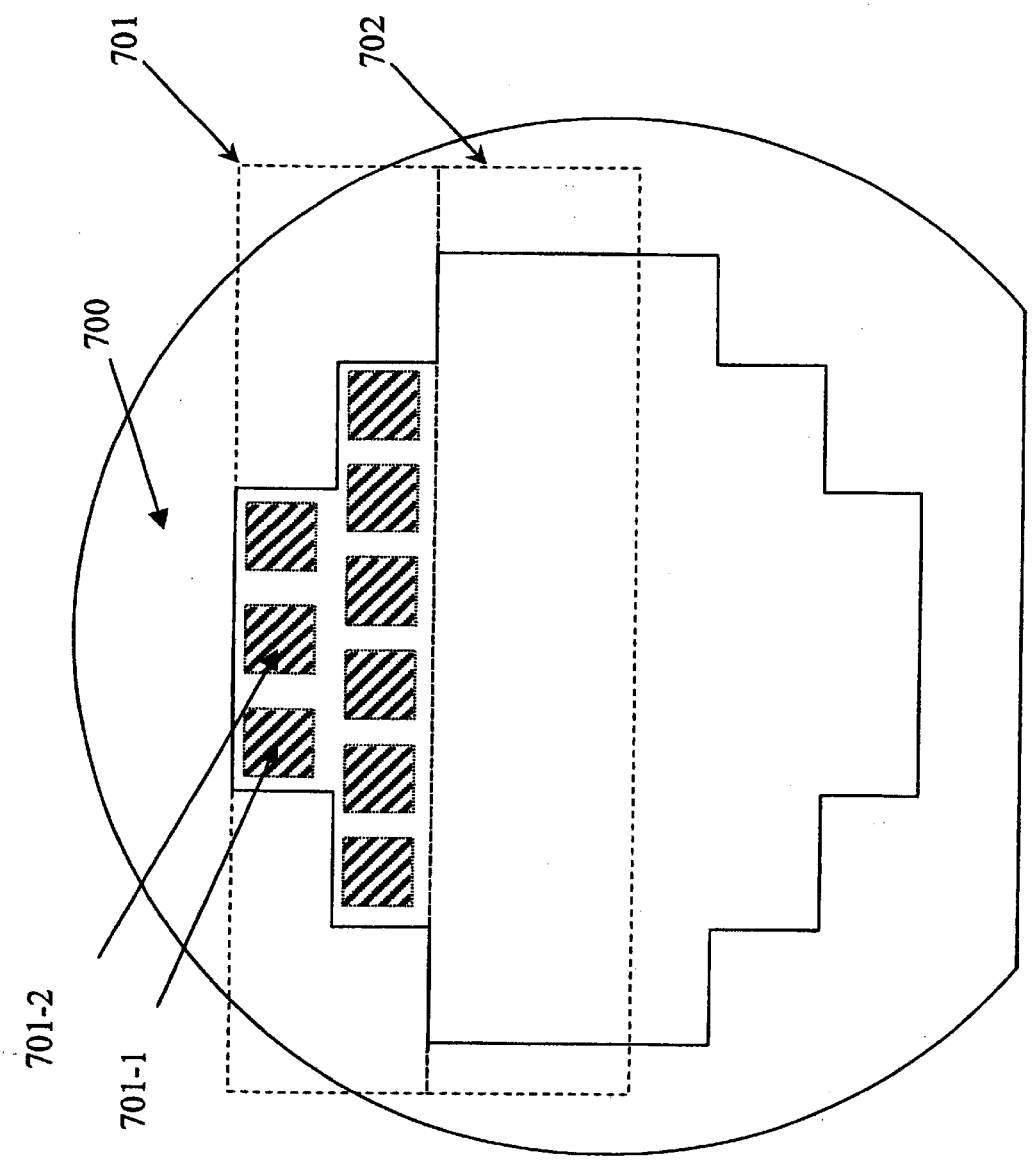
FIG. 7 illustrates the determination of portions of the target object surface requiring 3D imaging in a method in accord with the present invention.

The coordinated cooperative operation of the exemplary embodiments depicted in FIGS. 1-3 are now described with reference to FIG. 7. Target object region 701 is the first region on wafer 700 subject to 2D imaging such as by the techniques described with reference to FIGS. 5 and 6. When the 2D subsystem has completed data acquisition for region 701, that data is buffered for further processing. The region 701 2D data is processed in controller 1001 where two principal operations are performed. In accord with the present invention, the 2D data is processed to select those subregions of region 701 which require 3D scanning for verification of specification compliance. For example, in region 701 a pattern recognition algorithm might identify that subregions 701-1, 701-2, etc. contain solder balls. Verification of specification compliance for parameters amenable to only 2D data analysis alone, such as ball spacing in a flip chip or BGA device, may optionally be performed in addition.

At this point the acquisition of further data may proceed in alternative manners depending on the nature of the feature distribution and specification compliance requirements for the specific type of target objects as will now be explained. With further reference to FIG. 7, after the first 2D data is buffered for region 701, the 2D scanning assembly 100 may be directed to scan the next region 702, or alternatively, 3D scanning assembly 110 may be directed to scan region 701. This movement may be accomplished in a conventional manner by either translation of the target object or motion of the scanning assembly.

It will be observed that for many target objects, for example, a flip chip, the majority of the surface area is relatively flat and featureless. Therefore, the height, or Z, data for the featureless regions is useless and constitutes "filler" in the data set which needlessly consumes processing resources thereby slowing down the specification verification process. If there are numerous relatively closely spaced features requiring 3D imaging on the target object as in the case of a bumped wafer, the more efficient procedure usually will be for 3D scanning assembly 110 to scan all of region 701. Then using the results of the 2D data analysis of region 701, optical triangulation calculations will only be performed on subregions 701-1, 701-2, etc. of region 701 resulting in savings in time compared to performance of an optical triangulation calculation for entire region 701 in this embodiment of a method according to the invention. In such a circumstance, after the first set of 2D data is buffered, while that set of 2D data is being processed the 3D scanning proceeds to scan the previous 2D scanned region, here 701. Thereafter, with the results of the 2D scan available, the 3D scanning subsystem selectively processes only those portions of the 3D raw data which were previously identified as containing 3D features of interest. At the same time that the 3D data for region 701 is being processed, scanning assembly 100 resumes 2D scanning at region 702 and the cycles continue for subsequent regions until the entire wafer is imaged as required. After the initial 2D scan and until the last 3D scan, at any given moment, while one scanning subsystem is acquiring data, the other subsystem is processing its previously acquired data.

In another embodiment of a method in accord with the present invention, in a situation where the object features requiring full 3D imaging are likely to be few and relatively widely spaced, it would tend to be more time efficient to have scanning assembly 110 directed to scan only subregions 701-1, 701-2, etc. of region 701 resulting in savings in time compared to a full 3D scan of entire region 701. Then the optical triangulation calculation would only be performed for the selected subregions. Accordingly, in this embodiment, before the 3D scan may commence, the first set of 2D data must be processed to determine the subregions of interest for 3D scanning. So, in this embodiment of the method, after 2D data is acquired for the first region 701, that data is processed while 2D data for the next region 702 is buffered. After the first set of 2D data is processed to determine subregions of interest for 3D scanning, the first 3D scan of only the subregions of interest of region 701 may be scanned. Subsequently, the 2D scan of region 703 (not illustrated) may proceed. While the 3D scan of subregions 701-1, 701-2, etc. and the 2D scan of region 703 are in progress, the analysis of 2D data for region 702 may be performed. Accordingly, after the first two consecutive 2D scans and until the last region is analyzed, at any given moment one scanning subsystem may be scanning while the other system is analyzing data. In this alternate embodiment, the method in accord with the present invention can enhance speed and efficiency during both the scanning and imaging phases of specification verification.

The tradeoff in efficiency between the method embodiments relates to the fact that mechanical repositioning of the scanning assembly or target object may be relatively slow compared to the computational steps. Therefore if there are numerous closely spaced 3D target features, the time incurred in repositioning may obviate any potential savings from the reduction in surface area scanned. Conversely, when the 3D features are few and widely spaced the time involved in repositioning may be relatively small compared to the savings in measurement and analysis time. Also, the selection will depend on the relative mechanical and electronic response times and computational speed of the particular components selected. One of ordinary skill in the art with knowledge of the expected feature distribution and specification compliance requirements for the specific type of target objects and with the benefit of this disclosure can determine the optimum embodiment of the method for particular types of objects without undo experimentation.

It should be understood that the 2D scanning of each region will usually be completed in nearly the same amount of time each time it is executed. However, the 3D scanning of each region is completed in a variable amount of time since it depends upon the features of the region which require 3D scanning as determined by the previous 2D scan and the programmed selection criteria used to determine the subregions of interest. Since a 2D scan is usually completed more quickly than a 3D scan of the same region, the 2D scanning subsystem is capable of getting ahead of the 3D scanning subsystem depending on the memory resources of controller 1001. However, it may not be advantageous for the 2D subsystem to get very far ahead of the 3D subsystem since the rate limiting step is completion of the 3D scan. That is, since the system cannot move on to the next target object until the last subregion requiring 3D scan is completed, buffering lots of 2D data may provide no additional benefit. However, some buffering of 2D data would be advantageous if the target objects to be scanned will routinely have regions having few or no subregions requiring 3D scanning. In this situation, the 3D subsystem may be able to very rapidly deal with such low 3D interest regions. Accordingly, it would be advantageous for some amount of extra 2D data to be buffered so that 3D subsystem wait-time is minimized.

Figure 8:
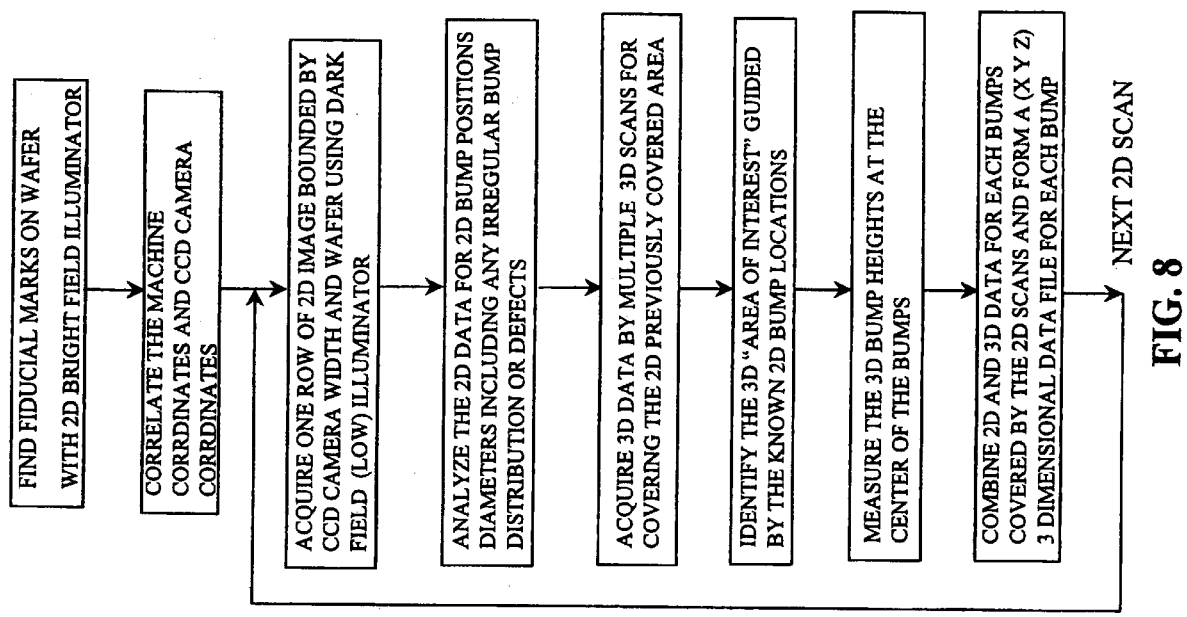
FIG. 8 is a flow chart illustrating a method of data acquisition and processing in accord with the present invention.

FIG. 8 is a flow chart illustrating a method in accord with the present invention for measurement of the balls, or bumps, on a flip chip device, a bumped wafer, or a BGA device.

It should be appreciated that various types of conventional optical detectors may be utilized in the scanning subsystems comprising systems and methods in accord with the present invention including various CCDs, e.g., line cameras and area array cameras and PSDs of both single the single and multiple channel type.

While the present invention has been particularly shown and described with reference to particular embodiments thereof, it will be understood by those skilled in the art that various changes in form and details may be made therein without departing from the spirit and scope of the invention.

What is claimed is:

1. A method for imaging an object, comprising the steps of:

scanning a selected region of the surface of an object with a 2D optical detector to obtain data corresponding to 2D features of the selected region of the surface;

generating a 2D image from the data corresponding to 2D features of the selected region of the surface;

scanning the selected region of the surface of an object with a 3D optical detector to obtain data corresponding to 3D features of the selected region of the surface; and generating a 3D image of portions of the selected region of the surface, the portions of the selected region being selected based upon the 2D image previously generated for the selected region.

2. The method of claim 1 wherein the 2D optical detector is a line scan camera.

3. The method of claim 1 wherein the 2D optical detector is an area array camera.

4. The method of claim 1 wherein the 3D optical detector is a PSD.

5. The method of claim 1 wherein the 3D optical detector is a single channel PSD.

6. The method of claim 1 wherein the 3D optical detector is a multi-channel PSD.

7. The method of claim 1 further comprising buffering of 2D image data from more than one selected region of the surface of an object before generating a 3D image of portions of the selected regions.

8. A method for imaging an object, comprising the steps of:

scanning a selected region of the surface of an object with a 2D optical detector to obtain data corresponding to 2D features of the selected region of the surface;

generating a 2D image from the data corresponding to 2D features of the selected region of the surface;

identifying portions of the selected region of the surface which contain features requiring 3D imaging from the 2D image;

scanning identified portions of the selected region of the surface of an object with a 3D optical detector to obtain 3D data corresponding to features of the identified portions of the selected region of the surface; and generating a 3D image of the identified portions of the selected region of the surface.

9. The method of claim 8 further comprising buffering of 2D image data from more than one selected region of the surface of an object before scanning portions of the selected regions with a 3D optical detector.

10. A system for imaging of objects comprising:

a 2D scanning assembly;

a 3D scanning assembly; and a controller, the controller having circuitry to direct imaging by the 3D scanning assembly based on analysis of imaging data from the 2D scanning assembly.

11. The system of claim 10 wherein scanning by the 3D scanning assembly is directed based on analysis of imaging data from the 2D scanning assembly.

12. The system of claim 10 wherein the controller has circuitry to direct independently the acquisition and processing of imaging data from either the 2D scanning assembly or the 3D scanning assembly.

13. The system of claim 10 where the 2D scanning assembly and the 3D scanning assembly are coaxially aligned.

14. The system of claim 10 where the 2D scanning assembly and the 3D scanning assembly are non-coaxially aligned.

15. The system of claim 10 where the 2D scanning assembly comprises a line camera.

16. The system of claim 10 where the 2D scanning assembly comprises an area array camera.

17. The system of claim 10 where the 3D scanning assembly comprises a PSD.

18. The system of claim 10 where the 3D scanning assembly comprises a single channel PSD.

19. The system of claim 10 where the 3D scanning assembly comprises a multichannel PSD.

* * * * *

UNITED STATES PATENT AND TRADEMARK OFFICE
CERTIFICATE OF CORRECTION

PATENT NO.    : 6,291,816 B1
DATED         : September 18, 2001
INVENTOR(S)   : Liu It is certified that error appears in the above-identified patent and that said Letters Patent is hereby corrected as shown below:

Column 6,
Line 9, change "9±9 and 1±20" to -- 9x9 and 1x20 --.

Signed and Sealed this

Fourth Day of June, 2002

Attest:

JAMES E. ROGAN
Attesting Officer                Director of the United States Patent and Trademark Office